United States Patent
Tumpold et al.

(10) Patent No.: US 11,415,559 B2
(45) Date of Patent: Aug. 16, 2022

(54) PHOTOACOUSTIC GAS SENSOR AND METHOD FOR DETERMINING GAS CONCENTRATION FROM COMMON POINT SLOPE ANALYSIS

(71) Applicant: Infineon Technologies AG, Neubiberg (DE)

(72) Inventors: David Tumpold, Munich (DE); Christoph Glacer, Munich (DE)

(73) Assignee: INFINEON TECHNOLOGIES AG, Neubiberg (DE)

( * ) Notice: Subject to any disclaimer, the term of this patent is extended or adjusted under 35 U.S.C. 154(b) by 324 days.

(21) Appl. No.: 16/654,087

(22) Filed: Oct. 16, 2019

(65) Prior Publication Data
US 2020/0041460 A1     Feb. 6, 2020

Related U.S. Application Data

(62) Division of application No. 15/791,132, filed on Oct. 23, 2017, now Pat. No. 10,551,356.

(51) Int. Cl.
*G01N 29/24* (2006.01)
*G01N 33/00* (2006.01)
*G01N 21/17* (2006.01)

(52) U.S. Cl.
CPC ..... *G01N 29/2418* (2013.01); *G01N 21/1702* (2013.01); *G01N 33/004* (2013.01); *G01N 2021/1704* (2013.01); *G01N 2291/021* (2013.01); *G01N 2291/02809* (2013.01)

(58) Field of Classification Search
CPC ........... G01N 29/2418; G01N 21/1702; G01N 33/004; G01N 2021/1704; G01N 2291/021; G01N 2291/02809
USPC .......................................................... 73/643
See application file for complete search history.

(56) References Cited

U.S. PATENT DOCUMENTS

| | | | |
|---|---|---|---|
| 3,938,365 A | 2/1976 | Dewey, Jr. | |
| 5,125,749 A | 6/1992 | Leugers et al. | |
| 5,373,457 A | 12/1994 | George et al. | |
| 5,753,797 A * | 5/1998 | Forster | G01N 21/1702 250/343 |
| 5,841,017 A | 11/1998 | Baraket et al. | |

(Continued)

OTHER PUBLICATIONS

Shen, Yaochun et al., "Time Resolved Aspects of Pulsed Photoacoustic Spectroscopy," Analytical Sciences, vol. 17, Special Issue, Apr. 2001, 2 pages.

*Primary Examiner* — Peter J Macchiarolo
*Assistant Examiner* — Monica S Young
(74) *Attorney, Agent, or Firm* — Slater Matsil, LLP

(57) ABSTRACT

A method for measuring the concentration of a gas includes heating a first gas with a pulse of light, the pulse of light having a wavelength absorbed by the first gas, wherein the first gas exerts pressure on a flexible membrane. The method includes receiving a first signal indicating a first deflection of the membrane, wherein the first deflection is due to a change in pressure of the first gas and receiving a second signal indicating a second deflection of the membrane occurring after the first signal, wherein the second deflection is due to the change in pressure of the first gas. The method includes determining a difference between the first signal and the second signal and, based on the difference between the first signal and the second signal, determining a first concentration of the first gas.

15 Claims, 12 Drawing Sheets

(56) References Cited

U.S. PATENT DOCUMENTS

| | | |
|---|---|---|
| 6,628,396 B1 | 9/2003 | Gul |
| 6,654,713 B1 | 11/2003 | Rethman et al. |
| 6,825,471 B1 * | 11/2004 | Shulga .............. G01N 21/1702 |
| | | 250/343 |
| 8,233,150 B2 | 7/2012 | Van Kesteren |
| 2014/0049770 A1 * | 2/2014 | Li ..................... A61B 5/0095 |
| | | 356/40 |
| 2015/0211983 A1 | 7/2015 | Speck et al. |
| 2015/0339807 A1 | 11/2015 | Beardsley et al. |
| 2017/0138951 A1 | 5/2017 | Murray et al. |
| 2017/0315051 A1 * | 11/2017 | Nagase ................. C23C 16/18 |
| 2019/0017893 A1 | 1/2019 | Tumpold |

* cited by examiner

PHOTOACOUSTIC GAS SENSOR AND METHOD FOR DETERMINING GAS CONCENTRATION FROM COMMON POINT SLOPE ANALYSIS

This application is a divisional of U.S. patent application Ser. No. 15/791,132, filed on Oct. 23, 2017, which application is hereby incorporated herein by reference.

TECHNICAL FIELD

The present invention relates generally to a system and method for a photoacoustic gas sensor, and, in particular embodiments, to a system and method for determining gas concentration from photoacoustic sensor signals.

BACKGROUND

Generally, the photoacoustic effect refers to a local change in the volume or pressure of a gas due to absorption of light. For instance, molecules of a particular gas may absorb particular frequencies of light, increasing the temperature of the molecules and causing the volume or pressure of the gas to correspondingly increase. A photoacoustic gas sensor uses the photoacoustic effect to determine properties of a gas such as its concentration or composition. In some cases, the signal from the photoacoustic gas sensor requires processing or analysis before useful information about the gas measurement can be determined.

SUMMARY

In accordance with an embodiment of the present invention, a method includes receiving a first output signal from a pressure sensor, the first output signal associated with a first concentration of a gas and receiving a second output signal from the pressure sensor, the second output signal associated with a second concentration of the gas. The method also includes determining a first slope of the first output signal from a first value of the first output signal at a first indication of time and a second value of the first output signal at a second indication of time and determining a second slope of the second output signal from a first value of the second output signal at the first indication of time and a second value of the second output signal at the second indication of time. The method also includes determining a correlation between the slope of an output signal and the concentration of the gas based on the first slope, the second slope, the first concentration, and the second concentration. In an embodiment, the first output signal and the second output signal have a same value at a third indication of time between the first indication of time and the second indication of time. In an embodiment, the gas is $CO_2$. In an embodiment, the pressure sensor is part of a photoacoustic sensor system. In an embodiment, the method further includes illuminating the gas with a periodically modulated light source. In an embodiment, the first indication of time and the second indication of time indicate times when the gas is not illuminated by the periodically modulated light source. In an embodiment, the pressure sensor comprises a flexible membrane, and the first output signal corresponds to an amount of deflection of the membrane. In an embodiment determining the correlation includes determining parameters of a linear relationship between the slope of an output signal and the concentration of the gas based on the first slope, the second slope, the first concentration, and the second concentration. In an embodiment, the method further includes receiving a third output signal from the pressure sensor, determining a third slope of the third output signal from a first value of the third output signal at the first indication of time and a second value of the third output signal at the second indication of time, and determining a third concentration of the gas associated with the third output signal based on the third slope and the correlation. In an embodiment, determining a third slope of the third output signal includes summing the third output signal with at least one additional output signal. In an embodiment, the method further includes comparing a difference between the first value of the third output signal and a first value of a fourth output signal with a threshold value.

In accordance with an embodiment of the present invention, a method includes heating a first gas with a pulse of light, the pulse of light having a wavelength absorbed by the first gas, wherein the first gas exerts pressure on a flexible membrane. The method also includes receiving a first signal indicating a first deflection of the membrane, wherein the first deflection is due to a change in pressure of the first gas, and receiving a second signal indicating a second deflection of the membrane occurring after the first signal, wherein the second deflection is due to the change in pressure of the first gas. The method also includes determining a difference between the first signal and the second signal, and, based on the difference between the first signal and the second signal, determining a first concentration of the first gas. In an embodiment, the first signal is a voltage signal and the second signal is a voltage signal. In an embodiment, the difference between the first signal and the second signal is determined by an analog circuit. In an embodiment, determining a first concentration of the first gas includes comparing the difference between the first signal and the second signal with a value stored in a look-up table. In an embodiment, the first deflection of the membrane occurs after or at the same time that the pulse of light occurs.

In accordance with an embodiment of the present invention, a photoacoustic gas sensor includes a chamber containing a first gas, a pressure sensor disposed in the chamber, the pressure sensor including a flexible membrane and configured to output an output signal indicating a deflection of the membrane, and an emitter configured to illuminate the first gas with light. The photoacoustic gas sensor also includes a control circuit coupled to the pressure sensor and the emitter. The control circuit includes a sampling circuit configured to sample a first value of an output signal of the pressure sensor after a first duration of time and configured to sample a second value of the output signal of the pressure sensor after a second duration of time, an analysis circuit configured to receive the first value and the second value and determine a correlation value from a difference between the first value and the second value, and a correlation circuit configured to receive the correlation value and determine a concentration of the first gas based on the correlation value and a predetermined correlation between correlation values and concentrations of the first gas. In an embodiment, the analysis circuit is an analog circuit. In an embodiment, the first gas is $CO_2$. In an embodiment, the predetermined correlation is a linear function relating correlation values and concentrations of the first gas.

BRIEF DESCRIPTION OF THE DRAWINGS

For a more complete understanding of the present invention, and the advantages thereof, reference is now made to the following descriptions taken in conjunction with the accompanying drawings, in which.

Corresponding numerals and symbols in different figures generally refer to corresponding parts unless otherwise indicated. The figures are drawn to clearly illustrate the relevant aspects of the preferred embodiments and are not necessarily drawn to scale. To more clearly illustrate certain embodiments, a letter indicating variations of the same structure, material, or process step may follow a figure number.

DETAILED DESCRIPTION OF ILLUSTRATIVE EMBODIMENTS

The making and using of various embodiments are discussed in detail below. It should be appreciated, however, that the various embodiments described herein are applicable in a wide variety of specific contexts. The specific embodiments discussed are merely illustrative of specific ways to make and use various embodiments, and should not be construed in a limited scope.

The present invention will be described with respect to preferred embodiments in a specific context, namely a system and method for determining properties of a gas using a photoacoustic sensor system. Some of the various embodiments described herein include analyzing a signal from a photoacoustic sensor system to determine the concentration of a gas. In embodiments of the present invention, a signal from a photoacoustic gas sensor is analyzed to provide a measurement of the concentration of a gas within a volume. The optical wavelength of a pulsed light source is tuned or filtered to an optical absorption peak of a certain species of gas. The molecules of the gas absorb the pulses of light, which increases the thermal energy of the molecules. Consequently, the pressure within the volume increases due to the increased thermal energy of the gas. Between pulses, the gas cools and the pressure within the volume decreases. An embodiment system includes a sensor having a flexible membrane disposed within the volume that generates an electrical signal indicating an amount of membrane deflection. As the pressure within the volume increases and decreases due to the pulses of light (i.e., due to photoacoustic effects), the changes in pressure cause deflection of the membrane. An embodiment system uses the values of the signal at two predefined points in time to determine the concentration of the gas in the volume. An embodiment system also uses measurements of two known concentrations of the gas within the volume to calibrate the system for all other concentrations of interest.

Figure 1:
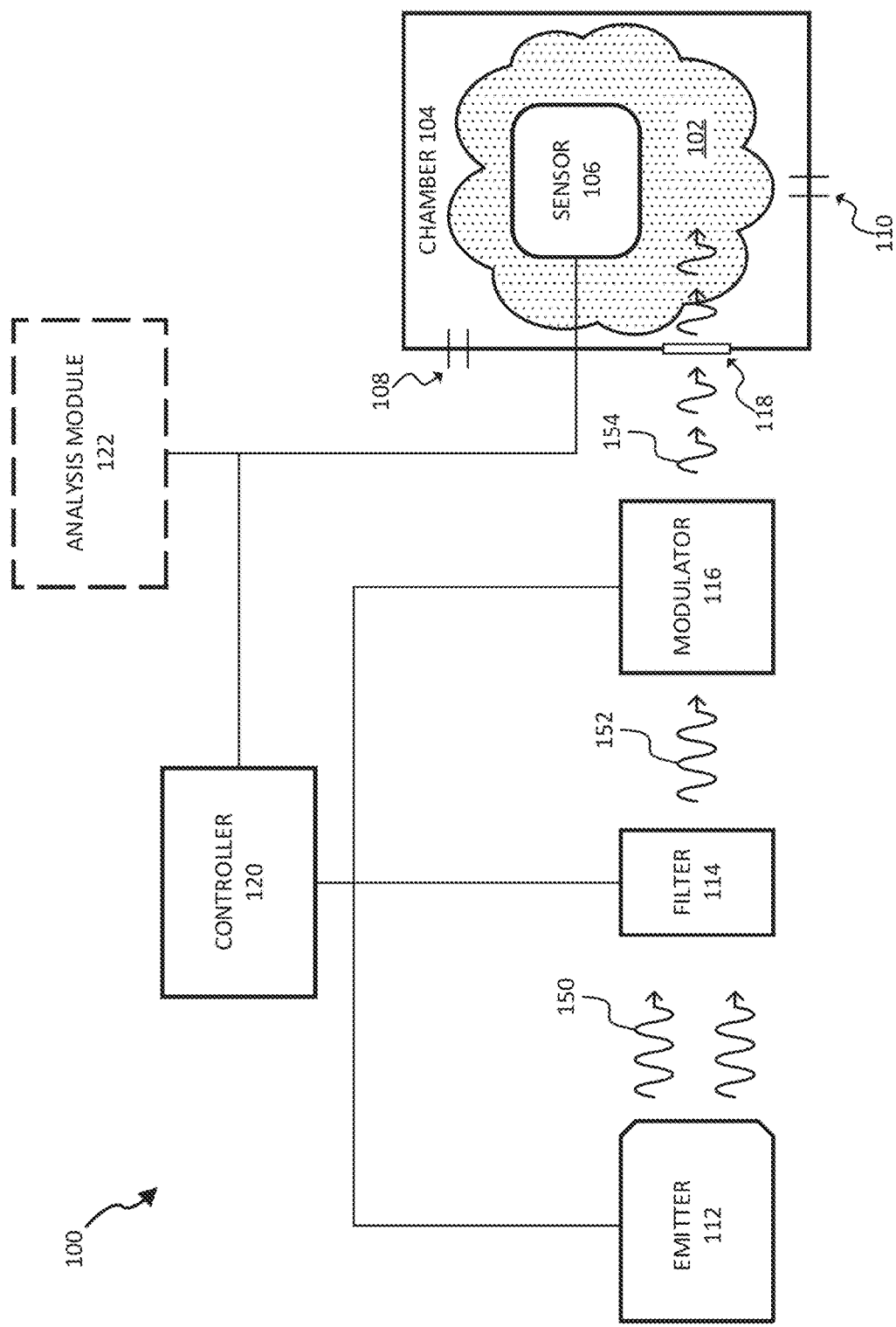
FIG. 1 illustrates a photoacoustic sensor system according to an embodiment.

FIG. 1 illustrates a schematic diagram of a photoacoustic sensor system 100 in accordance with an embodiment. The system 100 is configured to analyze a sample of a gas 102 using the photoacoustic effect. System 100 includes a chamber 104 that contains gas 102 and a photoacoustic sensor 106. Gas 102 may be, for example, a gas or a mixture of different types of gases having known characteristics (e.g., concentrations, proportions, composition, etc.) or gas 102 may be a gas or a mixture of different types of gases having unknown characteristics. Chamber 104 may be, for example, a housing or enclosure, and in some embodiments chamber 104 may be open to the environment. In some embodiments, chamber 104 may be open to the local atmosphere, and gas 102 may be the local atmosphere or a specific gas present in the local atmosphere. For example, system 100 may be configured to measure the concentration of $CO_2$ in the local atmosphere, though system 100 may be configured to measure concentrations of other gases in other embodiments. Chamber 104 may include one or more inlet ports 108 for admitting gaseous samples to be analyzed (e.g., gas 102) into chamber 104 and may also include one or more outlet ports 110 for venting chamber 104. In some cases, a single port (e.g., inlet port 108 or outlet port 110) may be used for both admitting a gas into chamber 104 and also venting chamber 104.

System 100 also includes an emitter 112 configured to generate light 150 that is absorbed by gas 102 to generate a photoacoustic effect. Emitter 112 may be, for example, a blackbody radiation source, a heater, an incandescent light source, a laser, a LED, another type of light source, or another source of electromagnetic radiation. In some cases, emitter 112 may be configured to generate light centered on one or more particular wavelengths and having narrow bandwidths (e.g. similar to a laser or LED), but in other cases, emitter 112 may be configured to generate light having a wider spectrum of wavelengths (e.g., similar to a blackbody emitter). Emitter 112 may emit light in an infrared (IR) spectrum, a visible spectrum, or in another spectrum, or in a combination of these.

In some embodiments, system 100 includes an optional filter 114 that filters wavelengths of light 150 generated by emitter 112. For example, filter 114 may include one or more optical filters that only allow particular wavelengths or bands of filtered light 152 to be transmitted through filter 114. In some embodiments, the wavelengths of filtered light 152 that filter 114 transmits may be changed. For example, a first part of filter 114 that transmits a first band of wavelengths may be exchanged for a second part of filter 114 that transmits a second band of wavelengths. In this manner, different combinations of individual filters within filter 114 may be configured for a particular gas or for a particular application. For example, the filtered light can have a particular wavelength that is absorbed by a first gas in chamber 104 much more than by other gases in chamber 104, and thus photoacoustic effects that are measured are mostly or entirely due to the first gas. In this manner, properties of a specific gas in a mixture of gases can be determined from photoacoustic measurements.

In some embodiments, the filtered light 152 is modulated in time by a modulator 116 to produce modulated light 154 that may be absorbed by gas 102. The modulator 116 may, for example, be a shutter or "chopper" that periodically blocks the filtered light 152. In some embodiments, emitter 112 generates modulated light 154 and no separate modulator 116 is used. For example, emitter 112 may be turned on and off to generate modulated light 154, or the power supplied to emitter 112 may be varied in time to generate modulated light 154. The modulated light 154 may be, for example, pulses of light, but in other cases the intensity of the light may be modulated in any suitable manner in time. For example, the light may be modulated in discrete pulses having a fixed duty cycle or a changing duty cycle. For example, the light may be modulated as discrete pulses having a duty cycle of 50% (i.e., as a square wave), or the light may be modulated with a duty cycle greater than 50% or less than 50%. In some embodiments, the light may be modulated sinusoidally, as a sawtooth wave, as a triangular wave, or modulated using another waveform. In some embodiments, pulses of modulated light 154 may have irregular periods or may have a constant period between individual pulses. The duration of the individual pulses of modulated light 154 may be constant or may be variable. In some embodiments, the period, modulation frequency, duty cycle, intensity, duration, or other characteristics of modulated light 154 may be adjusted between measurements. In some cases, the light 150 from emitter 112 may be modulated by modulator 116 before it is filtered by filter 114. In some embodiments, the modulation frequency may be between about 10 Hz and about 100 Hz, but other modulation frequencies may be used in other embodiments.

In some embodiments, a shorter duration of a pulse of light may be implemented by using a duty cycle less than 50%. Instead of using a higher modulation frequency in order to generate short pulses, a lower modulation frequency may be used with a smaller duty cycle to decrease the pulse duration. As an illustrative example, instead of using a 50% duty cycle at a modulation frequency of 10 Hz, the same pulse duration (50 ms) may be generated by using a 5% duty cycle at a modulation frequency of 1 Hz. In this manner, the generation of light pulses may be configured or optimized for tool performance, for system response time, to enhance filtering or noise reduction, for a particular application, or for other reasons.

In some embodiments, chamber 104 includes a window 118, and light (e.g., light 150, filtered light 152, or modulated light 154) may enter chamber 104 through window 118. In some cases, window 118 may be relatively transparent over a specific range of wavelengths (e.g., infrared wavelengths, visible wavelengths, etc.) In some cases, window 118 may filter light instead of or in addition to filter 114. In some embodiments, some or all of emitter 112, filter 114 (if present), or modulator 116 (if present) may be disposed within chamber 104.

In some embodiments, sensor 106 is a device configured to detect pressure and output a signal based on the pressure. For example, sensor 106 may output a voltage, a current, or a digital signal that indicates a pressure or a change in a pressure. In some embodiments, sensor 106 includes a membrane that deflects in response to a pressure differential between both sides of the membrane and outputs a signal based on the amount of deflection. In some embodiments, the membrane includes apertures that allow the pressure to equalize between sides of the membrane. Sensor 106 may include a membrane that is capacitively coupled such that the output signal represents a change in capacitance. In some embodiments, sensor 106 is a microphone or a microphone-like device. In some embodiments, sensor 106 includes one or more microelectromechanical systems (MEMS). Other types of pressure sensors or sensor structures may also be used and are within the scope of this disclosure. The operation of an example photoacoustic sensor 206 is described below with respect to FIGS. 2A-2E.

In some embodiments, system 100 includes a controller 120 that is electrically coupled to one or more of the sensor 106, emitter 112, filter 114, modulator 116, or other components of system 100. Controller 120 can, for example, send signals to operate, power, or monitor the components of 100. In some embodiments, controller 120 may include a specific application processor, a general microprocessor, a field programmable gate array (FPGA), a central processing unit (CPU), or discrete digital logic components. In some embodiments, controller 120 may be a control circuit.

In some embodiments, system 100 includes an optional analysis circuit 122 coupled to sensor 106. In some embodiments, analysis circuit 122 is configured to receive output signals from sensor 106 and perform processing operations on the output signals or portions of the output signals. The processing operations may include, for example, averaging or summing multiple output signals, performing analog-to-digital conversion of the output signal, comparing the output signal with values in a lookup table, storing one or more output signals, or other operations. In some embodiments, analysis circuit 122 is coupled to or is part of controller 120.

In some embodiments, controller 120 and analysis circuit 122 are formed on the same semiconductor substrate. In some embodiments, sensor 106 is a MEMS device, and is formed on the same semiconductor substrate as controller 120 or analysis circuit 122. In other embodiments, controller 120 or analysis circuit 122 are formed on a separate semiconductor substrate as sensor 106 and packaged together with sensor 106. Alternatively, sensor 106, controller 120, or analysis circuit 122 may be formed on separate semiconductor substrates and packaged in separate packages.

FIGS. 2A-2E illustrate an example measurement cycle of the operation of a photoacoustic sensor system 200 according to an embodiment. In particular, FIGS. 2A-2E illustrate the response of system 200 as a sample gas 204 is subjected to a pulse of light 220. Photoacoustic sensor system 200 may be similar to photoacoustic sensor system 100 described previously with respect to FIG. 1. System 200 includes a chamber 202 which contains gas 204 and pressure sensor 206. Chamber 202 may contain a mixture of gases including gas 204, but for this illustrative example the wavelength of light 220 is such that light 220 is only absorbed by gas 204, and as such only gas 204 is shown in FIGS. 2A-2E. In this example, pressure sensor 206 includes a flexible membrane 210 that separates a volume 208 from the greater interior 207 of chamber 202. Membrane 210 may include one or more apertures such as ventilation hole 211 that allow gas to flow between the greater interior 207 of chamber 202 and the volume 208. Chamber 202 also includes a port 212 that allows gas within volume 208 to be vented into or out of volume 208. In this example system 200, chamber 202 includes a window 218 through which light 220 (e.g., from an emitter such as emitter 112 described above) enters the chamber 202 and is absorbed by gas 204.

FIGS. 2A-2E also illustrate a diagram 230 indicating the relative deflection of membrane 210 over the measurement cycle. In some cases, this relative deflection correlates with an output signal transmitted from pressure sensor 206. For example, the relative deflection may correlate with a voltage output signal or a current output signal transmitted by pressure sensor 206, though in some cases the amplitude or polarity of an output signal may be different from that of the example relative deflection shown in diagram 230.

Figure 2A:
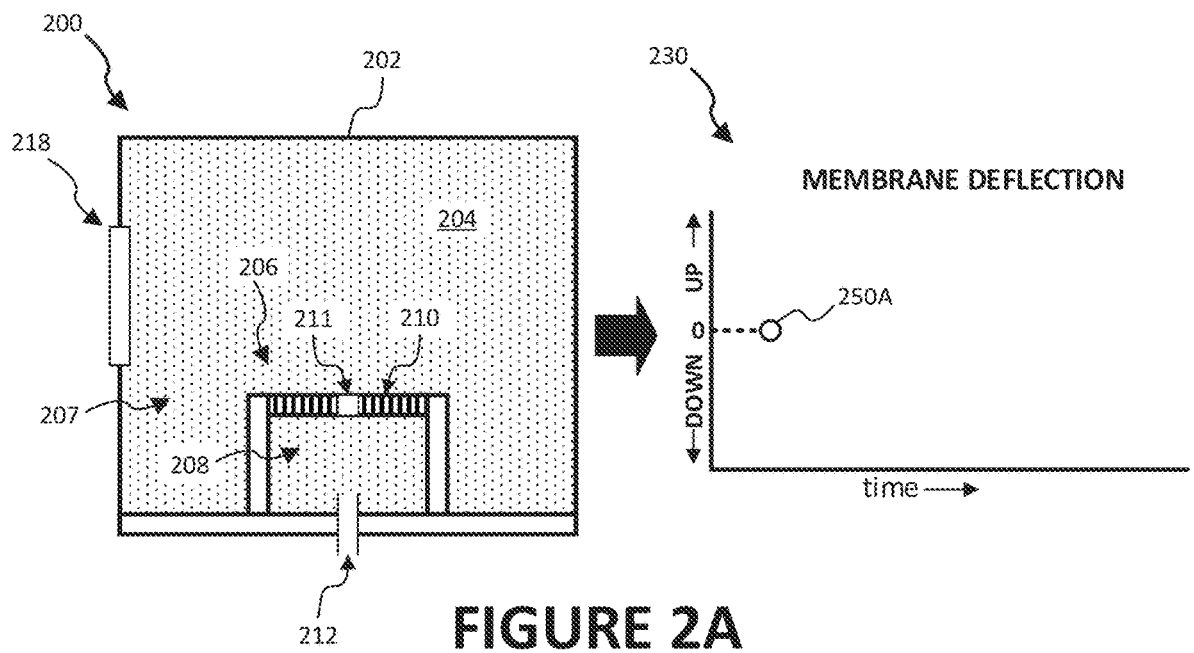
FIGS. 2A-2E illustrate a measurement cycle of the operation of a photoacoustic sensor system according to an embodiment.

Turning to FIG. 2A, FIG. 2A shows the system 200 in an equilibrium state during which light 220 is not impinging on gas 204. In FIG. 2A, the pressure of gas 204 in the greater interior 207 is approximately the same as the pressure of gas 204 in the volume 208. Since the pressure on each side of membrane 210 is approximately equal, membrane 210 is not deflected significantly upward or downward. This is shown in diagram 230 by point 250A in which the deflection is shown as zero.

Figure 2B:
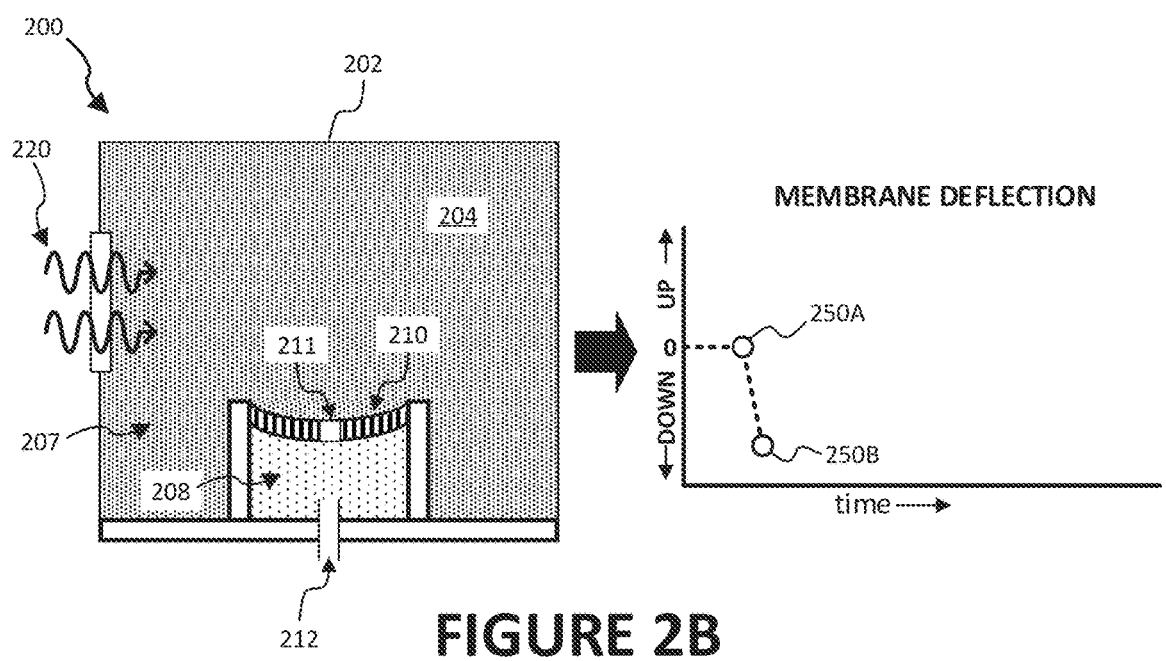

In FIG. 2B, light 220 is admitted into the greater interior 207 of chamber 202 and is absorbed by gas 204. As gas 204 absorbs the light 220, the temperature of gas 204 increases and so the pressure of gas 204 also increases in accordance with the ideal gas law:

$$PV=nRT \tag{1}$$

in which P is the pressure of the gas, V is the volume of the gas, n is the number of molecules of the gas, R is a gas-dependent constant, and T is the temperature of the gas. Although the apertures in membrane 210 allow gas 204 to flow from the greater interior 207 to the volume 208, this process is significantly slower than the photoacoustic response of the gas 204 upon illumination with light 220. Initially, the higher pressure of gas 204 in the greater interior 207 exerts a force on membrane 210 and deflects membrane 210 outwards, away from the greater interior 207. This is shown in diagram 230 by point 250B. In some cases, the amount of deflection of membrane 210 can indicate the amount, concentration, or proportion of gas 204 within chamber 202.

Figure 2C:
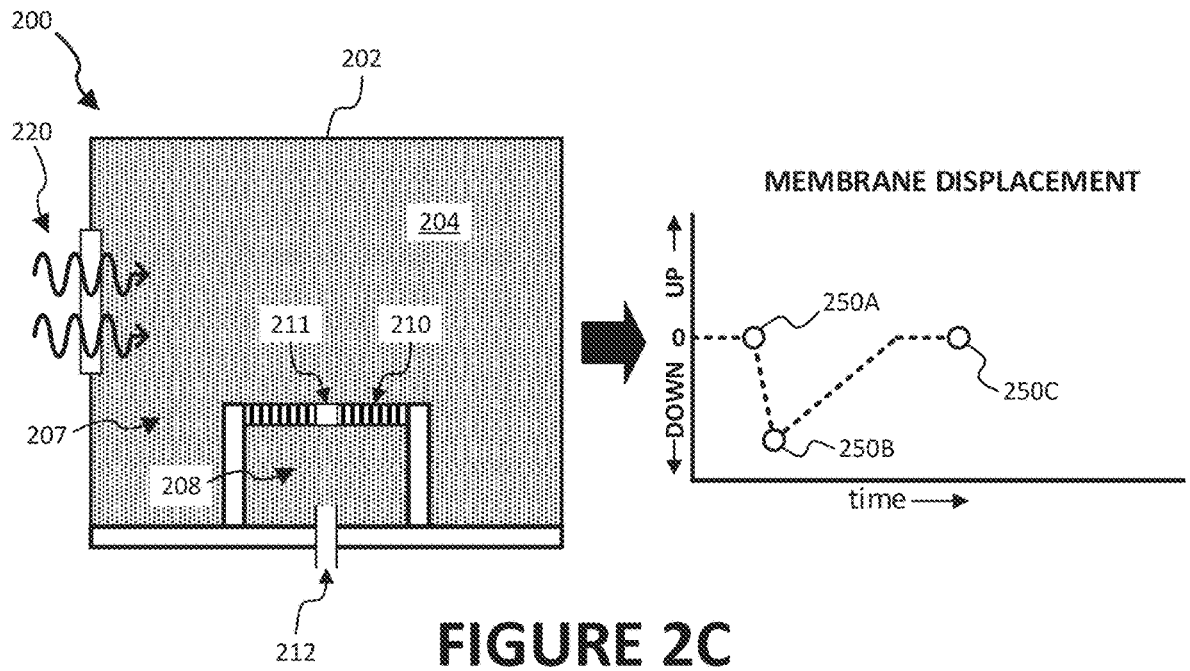

In FIG. 2C, light 220 continues to illuminate gas 204, but enough gas 204 has flowed from greater interior 207 into volume 208 that the gas 204 within greater interior 207 and the gas 204 within volume 208 have approximately the same pressure. In some cases, port 212 may also allow gas to flow into volume 208 and increase the pressure within volume 208. Accordingly, the forces exerted by pressure on both sides of membrane 210 are approximately equal, and membrane 210 has relaxed from having an outward deflection to having little or no deflection. As the particular operation or configuration of system 200 may vary depending on the application, in some cases light 220 may cease before membrane 210 fully relaxes. The relaxation of the membrane is shown in diagram 230 by point 250C. The sloping curve between points 250B and 250C shows the relaxation of membrane 210 as the pressure equalizes. In some cases, the shape of this sloping curve may depend on particular structural characteristics of membrane 210 or other components of system 200. In some cases, the shape of the sloping curve between points 250B and 250C can indicate the amount, concentration, or proportion of gas 204 within chamber 202.

Figure 2D:
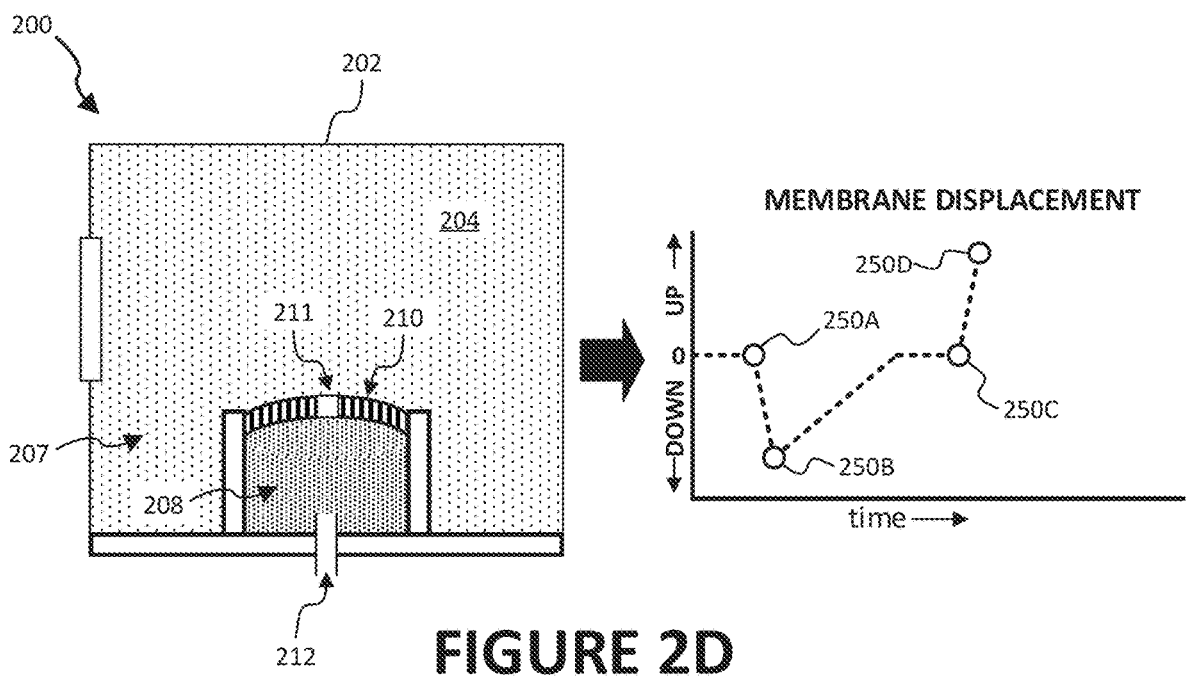

FIG. 2D illustrates system 200 shortly after the light 220 ceases illuminating gas 204. Without illumination, the gas 204 in greater interior 207 begins to cool and thus the pressure of the gas 204 within greater interior 207 decreases. However, the pressure of the gas 204 within volume 208 still remains at or near the higher pressure shown in FIG. 2C. This relatively higher pressure within volume 208 deflects membrane 210 inward, away from volume 208. This is shown in diagram 230 by point 250D. In some cases, the amount of deflection of membrane 210 can indicate the amount, concentration, or proportion of gas 204 within chamber 202.

Figure 2E:
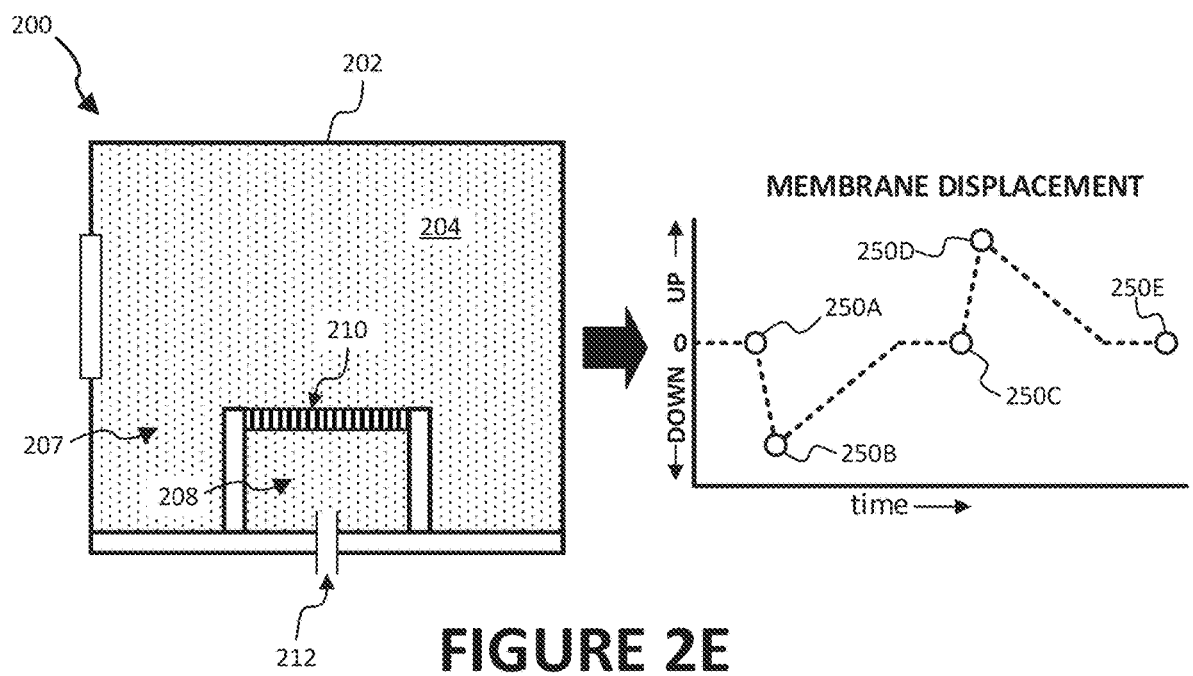

In FIG. 2E, enough gas 204 has flowed from volume 208 into greater interior 207 that the gas 204 within greater interior 207 and the gas 204 within volume 208 have approximately the same pressure. In some cases, port 212 may also allow gas to flow out of volume 208 and reduce the pressure within volume 208. Accordingly, the forces exerted by pressure on both sides of membrane 210 are approximately equal, and membrane 210 has relaxed from having an inward deflection to having little or no deflection. This is a similar condition to that shown in FIG. 2A. The relaxation of the membrane is shown in diagram 230 by point 250E. The sloping curve between points 250D and 250E shows the relaxation of membrane 210 as the pressure equalizes. In some cases, the shape of this sloping curve may depend on particular structural characteristics of membrane 210 or other components of system 200. In some cases, the shape of the sloping curve between points 250D and 250E can indicate the amount, concentration, or proportion of gas 204 within chamber 202. The process shown in FIGS. 2A-2E of heating gas 204 using light 220 and then allowing gas 204 to cool may be repeated as a measurement cycle, and portions of the signal from sensor 206 may be analyzed to provide information about gas 204.

Figure 3A:
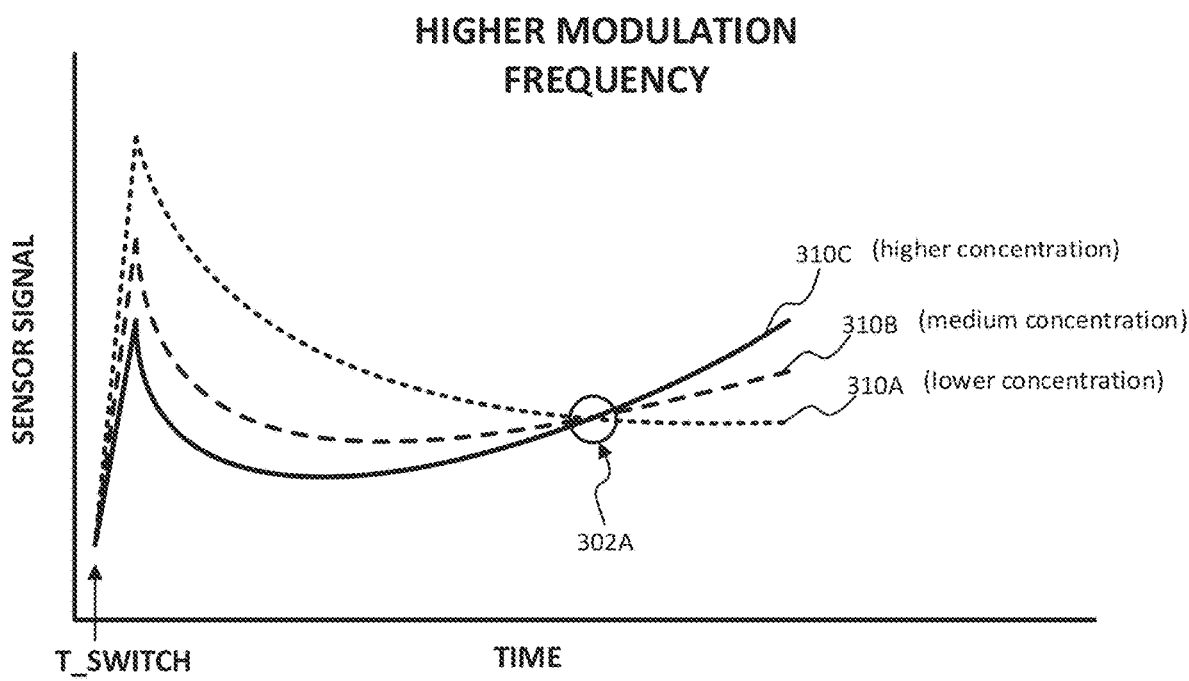
FIGS. 3A-3B illustrate sensor output signals of a pressure sensor of a photoacoustic sensor system according to an embodiment.
Figure 3B:
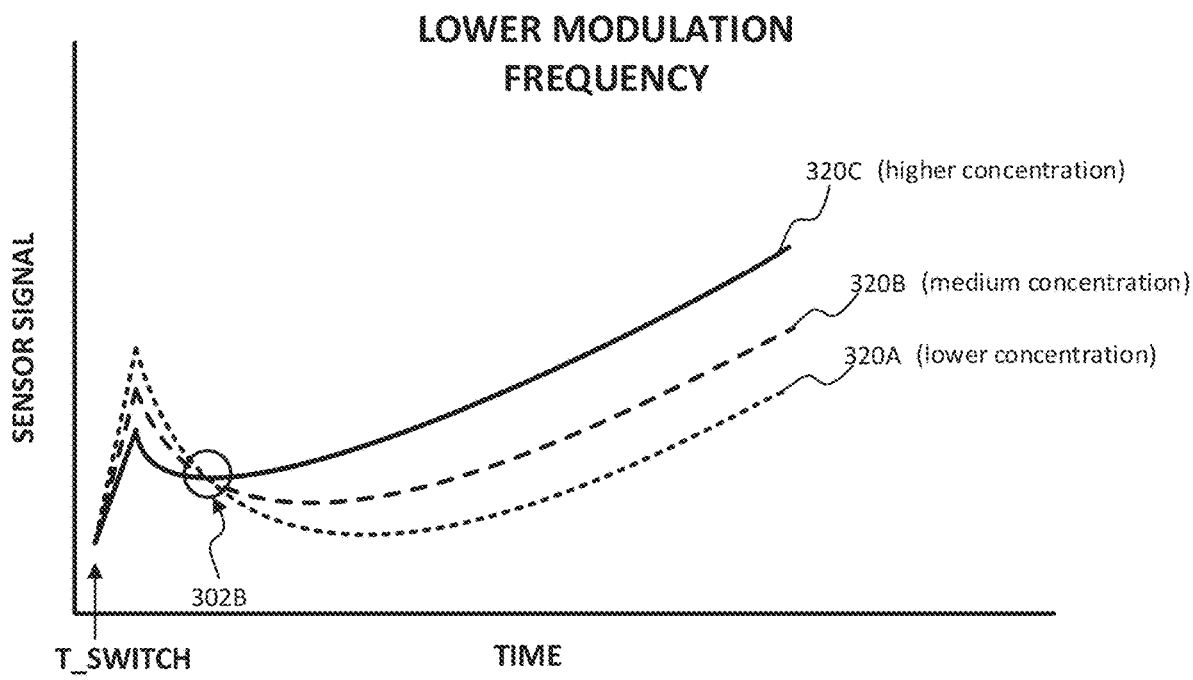

Turning now to FIGS. 3A-3B, FIG. 3A and FIG. 3B show representative example sensor output signals 310A-C and 320A-C, respectively, of a pressure sensor of a photoacoustic sensor system. FIG. 3A and FIG. 3B show example sensor output signals 310A-C and 320A-C starting from around a time T_SWITCH, which can represent the start of light illuminating a gas sample (heating the gas similar to FIG. 2B) or the cessation of light illuminating the gas sample (allowing the gas to cool similar to FIG. 2D), or another indication of time. The time between subsequent pulses of light used in FIG. 3A is shorter than the time between subsequent pulses of light used in FIG. 3B. As such, sensor output signals 310A-C of FIG. 3A have a higher modulation frequency than sensor output signals 320A-C of FIG. 3B. Each of signals 310A-C indicates a measurement of a different concentration of a gas, and each of sensor output signals 320A-C indicates a measurement of a different concentration of a gas. The signals 310A-C and 320A-C may be from a sensor similar to sensor 106 or sensor 206 described previously. Additionally, the signals 310A-C and 320A-C may be correlated with displacement of a membrane in a sensor, which may be similar to membrane 210 shown in FIGS. 2A-2E. Each of signals 310A-C and 320A-C may, for example, indicate a voltage over time or a current over time. In this example, the signals 310A-C and 320A-C are presented as the absolute value (magnitude) of the sensor output, and thus may represent the portion of the measurement cycle in which the illumination starts or the portion of the measurement cycle in which the illumination ceases.

As shown in FIG. 3A and FIG. 3B, the signals 310A-C and 320A-C increase relatively rapidly after time T_SWITCH. This rapid increase may be similar to the behavior of membrane 210 near points 250B or 250D shown in FIGS. 2A-2E. In other cases, as the membrane relaxes over time, a sensor output signal can have curved shapes similar to the example signals 310A-C and 320A-C shown in FIGS. 3A and 3B, but in other cases a sensor output signal may include linear portions or portions having different slopes or different shapes. As shown in FIGS. 3A and 3B, different concentrations of the gas sample can produce differently shaped sensor output signals. However, in some cases all of the sensor output signals for different gas concentrations intersect near a common point when superimposed or plotted together. This is shown in FIG. 3A by signals 310A-C intersecting near common point 302A and in FIG. 3B by signals 320A-C intersecting near common point 302B.

One feature of some sensor output signals shown by example signals 310A-C and 320A-C is that a higher concentration of gas produces a sensor output signal with a more positive slope near the common point, and a lower concentration of gas produces a sensor output signal with a more negative slope near the common point. For example, this behavior can be seen in FIG. 3A between signal 310A (associated with a measurement of a lower gas concentration) and signal 310C (associated with a measurement of a higher gas concentration). Near the common point 302A, signal 310A trends downward over time and thus has a negative slope, and signal 310C trends upward over time and thus has a positive slope. Thus, it is shown in FIGS. 3A and 3B that the slope of a portion of a sensor output signal may correlate with the concentration of the gas sample being measured.

A second feature of some sensor output signals that is shown by example signals 310A-C and 320A-C is that the position of the common point can be adjusted relative to T_SWITCH by adjusting the modulation frequency, waveform, or duty cycle of the light. For example, a higher modulation frequency can delay the position of the common point with respect to T_SWITCH relative to a lower modulation frequency. In some cases, changing the modulation frequency can change the shape or slope near the common point of a sensor output signal for a given gas concentration. For example, changing the modulation frequency may increase or reduce the value of the slope near the common point, including increasing a negative slope to a value above zero or decreasing a positive slope to a value below zero. However, changing the modulation frequency does not change the overall correlation between gas concentration and slope. This can be seen, for example, in measurements 300A and 300B in which the higher concentration signals 310C and 320C have different slopes near the common points at different modulation frequencies, but in each case the slopes of the higher concentration signals 310C and 320C near common point 302A are more positive than the slopes of the lower concentration signals 310A and 320A near common point 302B. In this manner, adjusting the modulation frequency can allow the position in time of the common point to be tuned according to the desired application.

Figure 4:
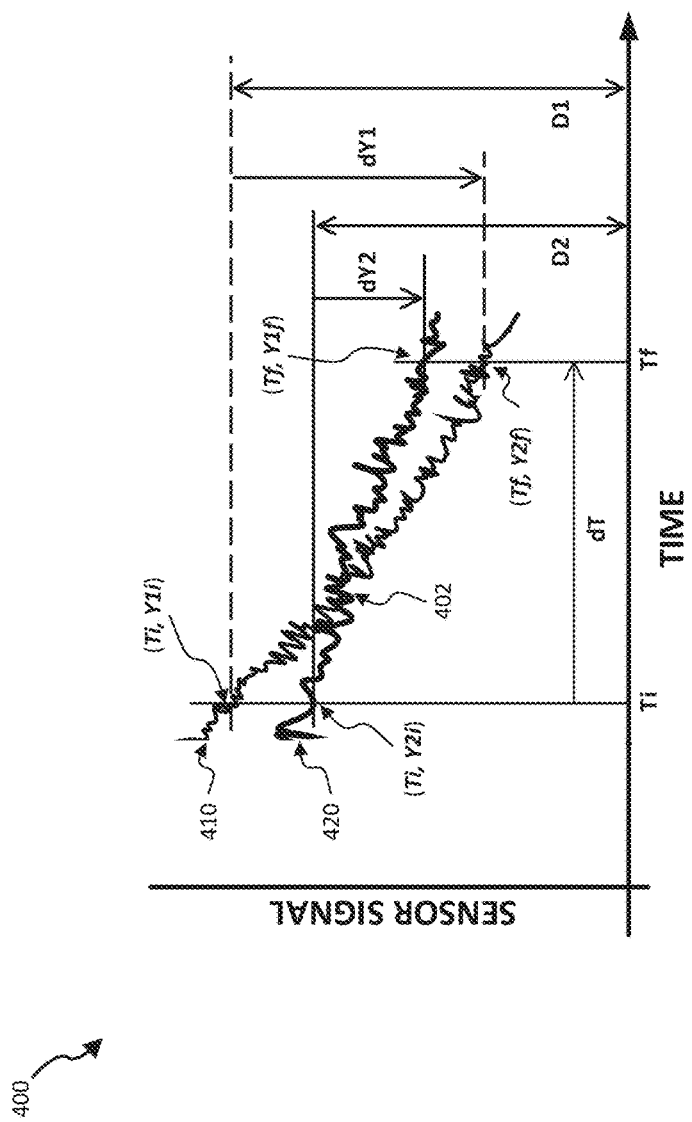
FIG. 4 illustrates a graph of example sensor output signals of a pressure sensor of a photoacoustic sensor system according to an embodiment.

Turning to FIG. 4, FIG. 4 shows a graph 400 of example sensor output signals 410 and 420 of a pressure sensor of a photoacoustic sensor system according to an embodiment. In this embodiment, signals 410 and 420 are the absolute value (magnitude) of the output signal of a sensor in a photoacoustic sensor system, such as those described previously. Signal 410 is associated with the measurement of a gas having a lower concentration, and signal 420 is associated with the measurement of the gas having a higher concentration. Signals 410 and 420 intersect near a common point 402, and for clarity graph 400 only shows portions of signals 410 and 420 near the common point 402. As described above with respect to FIGS. 3A and 3B, a slope of a portion of the sensor output signal can correlate with the concentration of the gas being measured. In this manner, a measurement of the slope can also provide an indication of gas concentration. For example, a slope of a first signal can be compared with a slope of a second signal around a similar time in the measurement cycle (e.g., near the common point), and the relative or absolute concentration of the gas associated with each signal can be determined. In some embodiments, the slopes of signals associated with known gas concentrations may be used to calibrate a photoacoustic sensor system, described in greater detail below with respect to FIG. 5.

In some embodiments, a sensor output signal approximately linear in a region near the common point, and the slope of this region may be approximated or calculated by sampling the sensor signal at two points separated in time near the common point. For example, signal 410 has a value Y1i at an initial time Ti and a value Y1f at a final time Tf. The slope K1 between these two points is given by:

$$K1 = \frac{(Y1f - Y1i)}{(Tf - Ti)} = \frac{dY1}{dT}. \quad (2)$$

Similarly, slope K2 of signal 420 is given by:

$$K2 = \frac{(Y2f - Y2i)}{(Tf - Ti)} = \frac{dY2}{dT}. \quad (3)$$

In some embodiments, the initial time Ti is before the common point 402 and the final time Tf is after the common point 402. In other embodiments, the initial time Ti and final time Tf may both be before the common point 402 or may be both after the common point 402. The choice of the initial time Ti and the final time Tf may be determined manually, be determined using an algorithm, may be determined based on one or more previous measurements, may be based on system parameters such as modulation frequency or duty cycle, may be determined in reference to another event time such as T_SWITCH, or may be determined or chosen based on other factors. In some embodiments, Ti and Tf may be equally separated in time around the common point 402, and in other embodiments, Ti and Tf may have different separations from the common point 402. In some embodiments, the same Ti and Tf are used for determining slopes of different sensor output signals, but in other embodiments, Ti or Tf may be different when determining a slope of a different sensor output signal.

In some embodiments, more than two points on a signal may be used to determine a slope. For example, a linear regression technique may be used to determine a slope using two or more points. In some embodiments, using only two points to determine a slope is sufficient for the accuracy desired in an application. In some embodiments, the signals from multiple measurement cycles may be summed together or averaged together to improve the signal-to-noise ratio before determining the slope. For embodiments in which the time difference dT used to determine the slope is constant, a concentration may be correlated with the signal difference (e.g., dY1 or dY2) across dT rather than with the slope across dT. Correlating the signal difference with concentration rather than correlating the slope with concentration may eliminate the need for division by dT and thus reduce the number of data processing steps.

Figure 5:
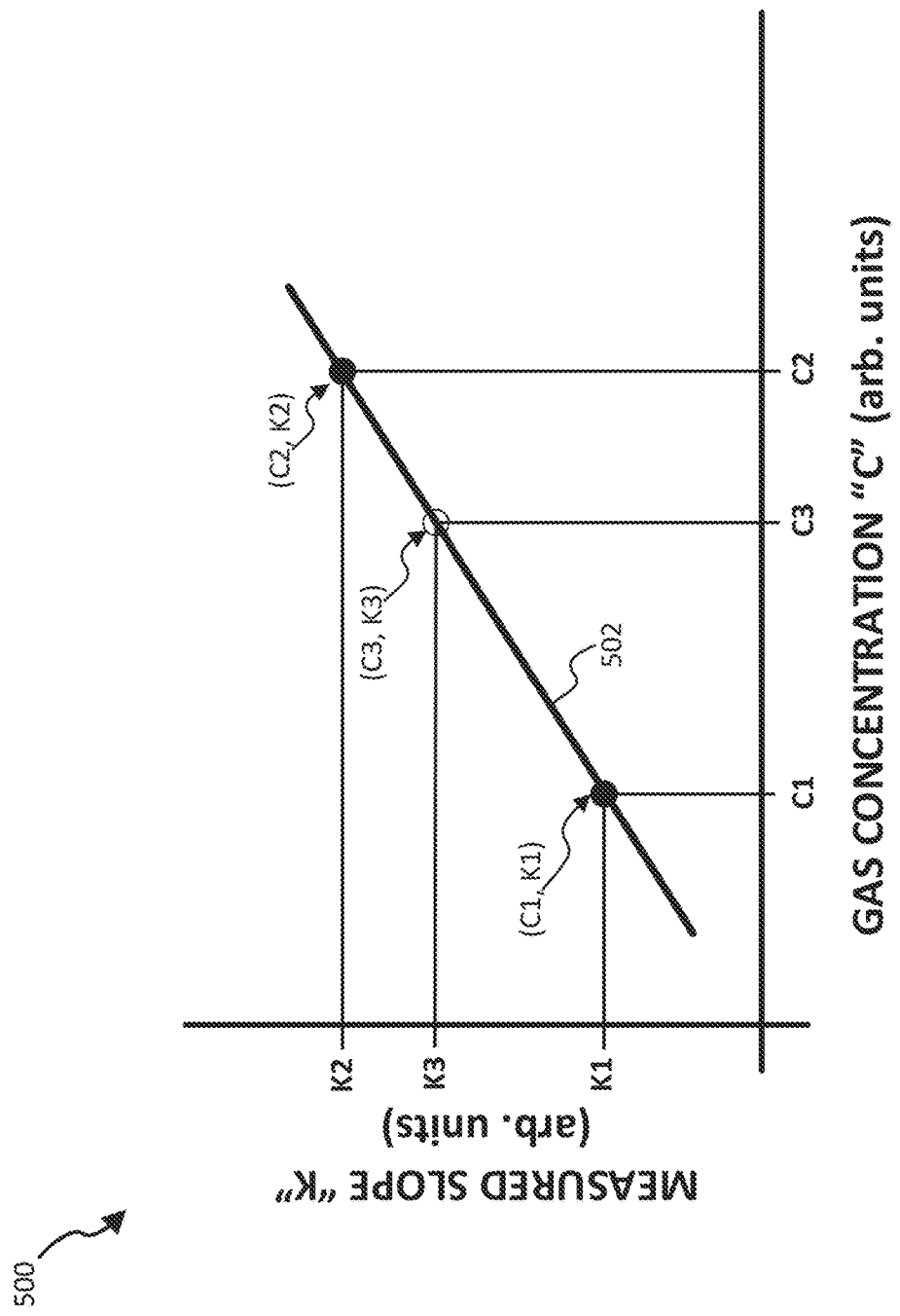
FIG. 5 illustrates a graph of an example curve plotting the slope of a sensor output signal versus the concentration of a gas sample according to an embodiment.

FIG. 5 illustrates a graph 500 of an example curve 502 plotting the slope of a sensor output signal ("K") versus the concentration of a gas sample ("C") according to an embodiment. As described above with respect to FIGS. 3A-3B and FIG. 4, the slope K of a sensor output signal correlates to the concentration C of the gas sample. In some cases, the relationship between K and C is linear function or an approximately linear function, as shown by curve 502 in FIG. 5. Therefore, if two slopes K1 and K2 are determined from measurements of two known concentrations of gas C1 and C2, respectively, the linear relationship between slope K and concentration C may be determined from an equation of a line:

$$K = mC + b = \left(\frac{K2 - K1}{C2 - C1}\right)C + b \quad (4)$$

in which m is the slope of the curve 502 and b is the y-intercept of the curve 502. Both the slope m and the y-intercept b may be determined from the two known points (C1, K1) and (C2, K2). Thus, from two measurements of a gas having different known concentrations, a photoacoustic sensor system can be calibrated such that an unknown concentration of the gas may be determined from a single measurement of that gas. For example, using the curve 502 determined from points (C1, K1) and (C2, K2), a measurement of slope K3 can be substituted for K in Equation 4 and the concentration C3 of the gas may be found. The slopes K1, K2, and K3 may be determined using the techniques described previously with respect to FIG. 4. In some embodiments, one of the known concentrations (C1 or C2) used to determine curve 502 may be the atmosphere. In some embodiments, curves such as curve 502 may be determined for more than one particular gas or for combinations of particular gases that a photoacoustic sensor system can measure. In this manner, a photoacoustic sensor system can be calibrated for multiple gases or for different applications. In some cases, the correlation between slope and concentration may not vary significantly between different units of a type of photoacoustic sensor system. As such, a curve 502 determined using one unit of a photoacoustic sensor system type may be used for other units of that type without determining a curve 502 for each separate unit.

In some embodiments, more than two points may be used to determine curve 502. For example, a linear regression technique or a partial linear regression technique may be used to determine curve 502 using two or more measurements of known gas concentrations. In some embodiments, curve 502 may be determined or represented using a piecewise-linear approximation, a polynomial approximation, curve-fitting techniques, or other approximation techniques. In some embodiments, using only two points to determine curve 502 is sufficient for the accuracy desired in an application. In some embodiments, the slopes found from multiple measurements of a single gas concentration may be summed together or averaged together to improve the signal-to-noise ratio before determining curve 502. In some cases, curve 502 may be less linear at higher values of concentration C, and approximation techniques described above may be used to approximate or otherwise represent a nonlinear portion of the curve 502.

Figure 6:
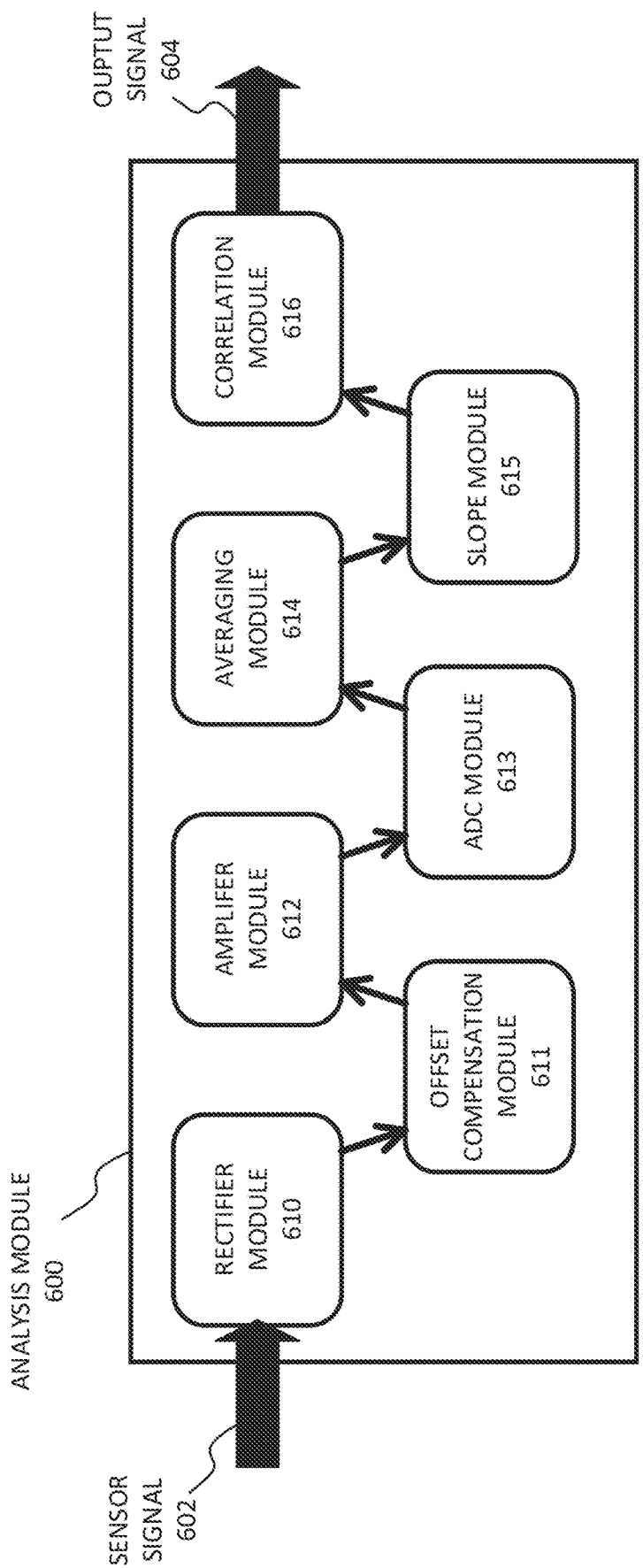
FIG. 6 illustrates an analysis circuit for a photoacoustic sensor system according to an embodiment.

FIG. 6 illustrates an analysis circuit 600 according to an embodiment. Analysis circuit 600 receives and analyzes sensor signals 602 from a photoacoustic sensor system and generates output signals 604. The sensor signals 602 may be raw signals or preprocessed signals, and may be, for example, a voltage or a current. The output signals 604 may represent the concentration or amount of a particular gas that is sensed by the photoacoustic sensor system. Analysis circuit 600 may be similar to analysis circuit 122 described with regard to FIG. 1, and may be part of or separate from a processor circuit (not shown). The example analysis circuit 600 shown in FIG. 6 includes multiple subcircuits 610-616 that operate on sensor signal 602. In some cases, subcircuits may be combined, duplicated, omitted, or operate in a different order or different manner than that shown in FIG. 6. Other subcircuits may be present than those shown in FIG. 6.

In an embodiment, rectifier subcircuit 610 receives the sensor signal 602 and outputs a rectified signal. For example, rectifier subcircuit 610 may output the absolute value (magnitude) of sensor signal 602 such that the rectified signal includes only positive values. Rectifier subcircuit 610 may be implemented, for example, by a circuit using diodes to provide rectification, though other types of circuits may also be used. Offset compensation subcircuit 611 receives the rectified signal and outputs an offset signal. For example, offset compensation subcircuit 611 may subtract a constant value from the rectified signal such that the minimum value of the offset signal is at or nearer to zero than the minimum value of the rectified signal, and that the maximum value of the offset signal is less than the maximum value of the rectified signal. Offset compensation subcircuit 611 may be implemented, for example, by a level shifter circuit that provides an appropriate voltage offset or an amplifier circuit using negative feedback that corrects for an offset, though other types of circuits may also be used. Amplifier subcircuit 612 receives the offset signal and outputs an amplified signal. For example, amplifier subcircuit 612 may multiply or scale the offset signal by a constant value to generate the amplified signal. Amplifier subcircuit 612 may be implemented, for example, by an op-amp circuit using negative feedback that amplifies and/or offsets the signal. In some embodiments, some or all of subcircuits 610-612 operate using analog techniques.

Analog-to-digital conversion (ADC) subcircuit 613 receives the amplified signal from amplifier subcircuit 612 and outputs a digital signal. For example, ADC subcircuit 613 may convert the values of the amplified signal into corresponding digital values that may be stored in a memory circuit (not shown) or processed using digital techniques. ADC subcircuit 613 may be implemented by a circuit using known ADC techniques, such as ADC using sigma-delta ADC techniques, SAR ADC techniques, or other types of ADC circuits or techniques. Averaging subcircuit 614 receives the digital signal and outputs an averaged signal. For example, averaging subcircuit 614 may average multiple digital signals from multiple measurement cycles together. Averaging subcircuit 614 may be implemented, for example, by a software algorithm run by a processor that sums digital signal values of multiple measurements at each discrete instance of time and then divides the sum by the number of summed values. In some embodiments, averaging subcircuit 614 sums multiple digital signals together and does not perform a division operation. In this manner, the number of operations may be reduced while still reducing the signal-to-noise ratio. In some cases, averaging subcircuit 614 may perform other types of processing (e.g., filtering the data, determining median values, etc.) to reduce noise, which may be implemented by appropriate software algorithms.

Slope subcircuit 615 receives the averaged signal and determines a slope of a portion of the averaged signal to generate a slope signal. Slope subcircuit 615 may determine a slope using the techniques described previously with respect to FIG. 4. For example, slope subcircuit 615 may use two points of the averaged signal and determine a slope between the two points. The time values of a point may represent an indication of time associated with that point.

Time values of the points may be predetermined in advance or be determined from one or more measurements. In some cases, the points may be taken from an illuminated part of the measurement cycle (e.g., similar to FIG. 2C) or from an unilluminated part of the measurement cycle (e.g., similar to FIG. 2E), or from more than one part of the measurement cycle. In some embodiments, the slope subcircuit 615 outputs the difference between the averaged signal values of the two points and does not divide by the difference in time values of the two points. In this manner, the number of operations may be reduced. The slope signal may be a digital signal that corresponds to a value of the determined slope. Slope subcircuit 615 may be implemented, for example, by a software algorithm run by a processor that stores the values of the points and performs operations on the values.

In some embodiments, slope subcircuit 615 may also reject signals deemed to be potentially inaccurate or excessively noisy. For example, slope subcircuit 615 may store the value of the first point of the previously received averaged signal (Ai[n−1]) and compare this previous value (Ai[n−1]) with the current value of the first point of the averaged signal value (Ai[n]). If the absolute difference between the previous value and the current value (|Ai[n−1]−Ai[n]|) is above some threshold value, slope subcircuit 615 may reject or ignore the current average signal. Other signal rejection techniques may be used, such as comparing other points, multiple points, slopes, or other characteristics of processed signals. In some embodiments, a similar technique of signal rejection may be implemented in one or more other subcircuits, such as by ADC subcircuit 613, averaging subcircuit 614, or another subcircuit. In some cases, the signal rejection is performed by a subcircuit other than slope subcircuit 615.

Correlation subcircuit 616 receives the slope signal from slope subcircuit 615 and, based on the slope signal, generates an output signal 604 representing a concentration or amount of gas. In some embodiments, correlation subcircuit 616 uses the techniques described above with respect to FIG. 5 to generate output signal 604. For example, correlation subcircuit 616 may use a value of the slope signal and correlate this value to a concentration of gas. Correlation subcircuit 616 may be implemented, for example, by a software algorithm run by a processor that stores values of the slope signal and performs operations on the values. For example, correlation subcircuit 616 may include a look-up table, algorithm, equation, function, or other data stored in a memory circuit that represents a slope-concentration correlation for the gas, which may be similar to the slope-concentration curve 502 shown in FIG. 5. In some cases, correlation subcircuit 616 may be used to determine the slope and concentration points that the slope-concentration correlation is determined from. In some cases, correlation subcircuit 616 may also generate a slope-concentration correlation and may store this correlation (e.g., in a memory circuit) for subsequent use. Output signal 604 may be an analog signal or a digital signal that represents a concentration or amount of gas associated with the photoacoustic sensor system. For example, output signal 604 may be a digital signal representing a numerical value of the parts-per-million (ppm) concentration of a particular gas.

Figure 7:
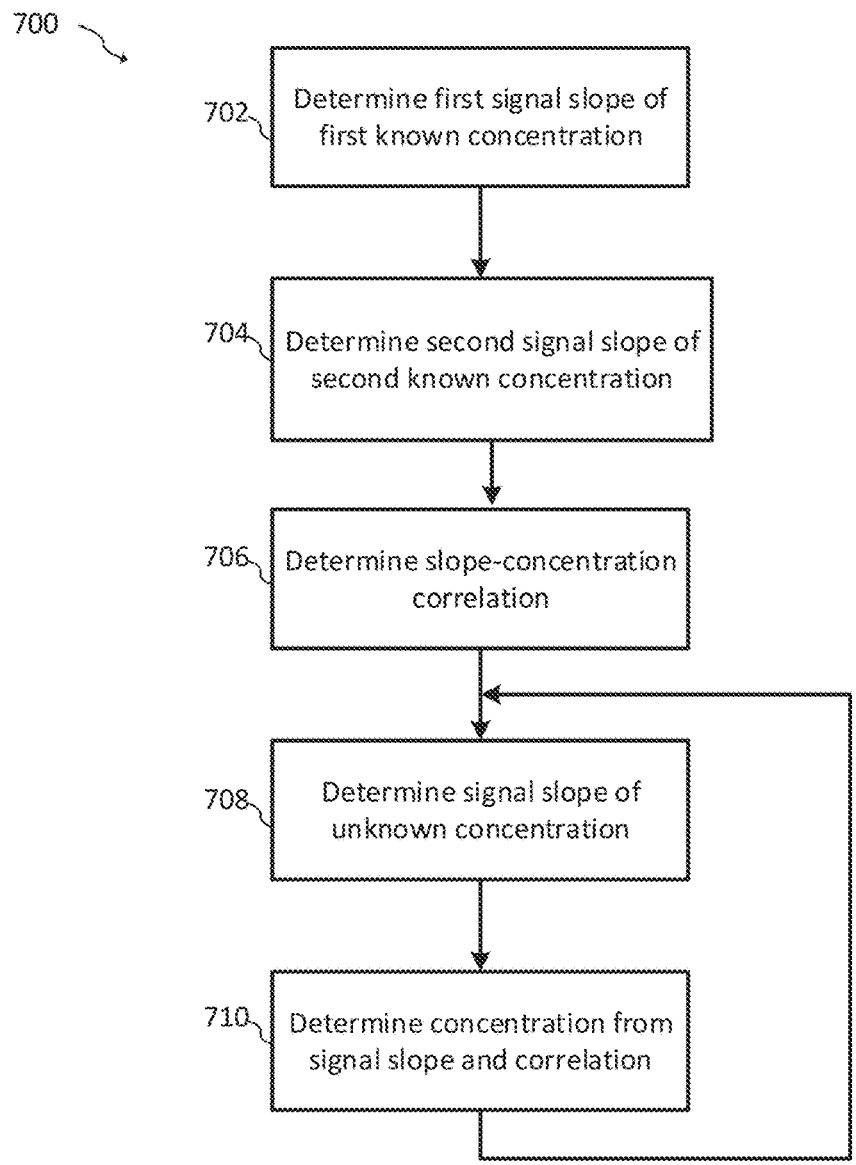
FIG. 7 illustrates a flowchart of a method for determining the concentration of a gas using a photoacoustic sensor system according to an embodiment.

FIG. 7 illustrates a flowchart of a method 700 for determining the concentration of a gas using a photoacoustic sensor system according to an embodiment. In some embodiments, the photoacoustic sensor system is similar to photoacoustic sensor system 100 shown in FIG. 1. Starting at step 702, a first slope of a first signal from the photoacoustic sensor system is determined, in which the first signal is output from the photoacoustic sensor system while measuring a first known concentration of a gas. The first slope may be measured using techniques described above, particularly with respect to FIG. 4. At step 704, a second slope of a second signal from the photoacoustic sensor system is determined, in which the second signal is output from the photoacoustic sensor system while measuring a second known concentration of the gas. The second slope may be measured using techniques described above, particularly with respect to FIG. 4. At step 706, the first slope, first gas concentration, second slope, and second gas concentration are used to determine a correlation between slope and concentration. The correlation may be linear, and may be determined using techniques described above, particularly with respect to FIG. 5. At step 708, a third slope of a third signal from the photoacoustic sensor system is determined, in which the third signal is output from the photoacoustic sensor system while measuring an unknown concentration of the gas. The third slope may be measured using techniques described above, particularly with respect to FIG. 4. At step 710, the correlation determined in step 706 is used to determine the concentration of the gas from the third slope. The concentration of the gas may be determined from the third slope using techniques described above, particularly with respect to FIG. 7. After step 710, steps 708 and 710 may be repeated, using the slopes of subsequent signals to determine concentrations of the gas subsequently measured by the photoacoustic sensor system.

Figure 8:
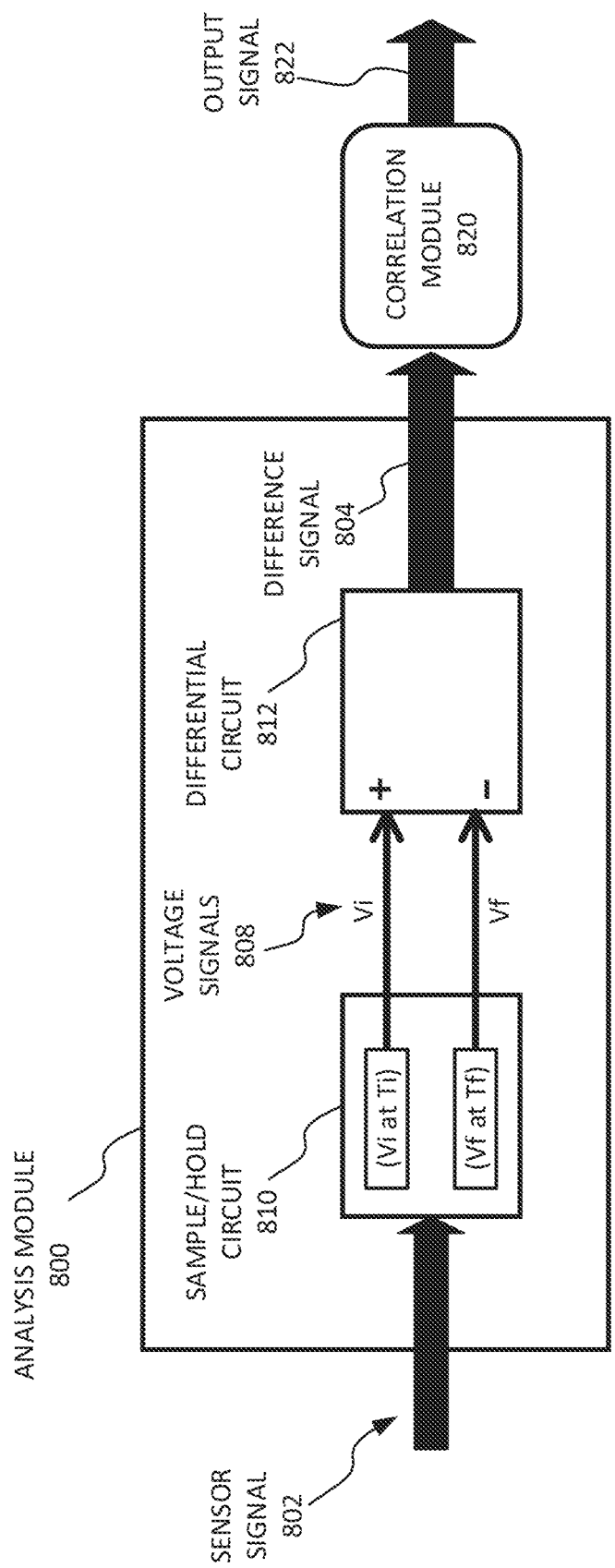
FIG. 8 illustrates another analysis circuit for a photoacoustic sensor system according to an embodiment.

FIG. 8 illustrates an analysis circuit 800 according to an embodiment. Analysis circuit 800 receives analog sensor signals 802 from a photoacoustic sensor system and generates analog output signals 804. The sensor signals 802 may be raw signals such as a voltage. Analysis circuit 800 may be similar to analysis circuit 122 described with regard to FIG. 1, and may be part of or separate from a processor circuit (not shown). In some embodiments, analysis circuit 800 may be implemented by one or more analog circuits. The example analysis circuit 800 shown in FIG. 8 includes a sample/hold circuit 810 coupled to a differential circuit 812. In some cases, other circuits or circuits may be present in addition to or instead of those shown in FIG. 8.

In some embodiments, sample/hold circuit 810 receives a sensor signal 802. Sample/hold circuit 810 is configured to sample sensor signal 802 at an initial time Ti and hold the voltage Vi of the sensor signal 802 at the initial time Ti. The voltage Vi at initial time Ti may, for example, correspond to or be similar to the points at (Ti, Y1i) or (Ti, Y2i) shown in FIG. 4. Sample/hold circuit 810 then samples sensor signal 802 at a final time Tf and holds the voltage Vf of the sensor signal 802 at that final time Tf. The voltage Vf at final time Tf may, for example, correspond to or be similar to the points at (Tf, Y1f) or (Tf, Y2f) shown in FIG. 4. In some embodiments, initial time Ti and final time Tf may be predetermined. In some cases, initial time Ti and final time Tf may be determined relative to a switching time or relative to a triggering signal. Sample/hold circuit 810 may output held voltage signals 808 corresponding to Vi and Vf.

In some embodiments, the voltage signals 808 are received by differential circuit 812. Differential circuit 812 is configured to determine a voltage difference (Vf−Vi) between the voltage signals 808 and generate a difference signal 804, which may be a voltage the same as the voltage difference or proportional to the voltage difference. As described previously with respect to FIG. 4, in some embodiments the difference between two signal values (e.g., between two signal voltages) at predetermined times can correlate with a concentration of gas. In this manner, analysis circuit 800 may be configured such that the difference signal 804 correlates with the concentration of a gas measured by a photoacoustic sensor system. Differential circuit 812 may be implemented, for example, by a circuit using a differential amplifier with feedback that provides a differential voltage output, though other types of circuits may also be used.

In some embodiments, difference signal 804 is then received by another circuit or circuit such as a correlation circuit 820. Correlation circuit 820 may be configured to receive difference signal 804 and generate an output signal 822 that represents a concentration or amount of gas. Correlation circuit 820 may be configured to use techniques such as those described with respect to FIG. 5 to generate output signal 822 from difference signal 804. In some embodiments, correlation circuit 820 may include portions of analysis circuit 600 or be similar to portions of analysis circuit 600, described above with respect to FIG. 6. In some embodiments, the use of analog techniques such as those described with respect to FIG. 8 to analyze a photoacoustic sensor signal can reduce signal processing operations or reduce the time it takes to analyze the sensor signal.

Figure 9:
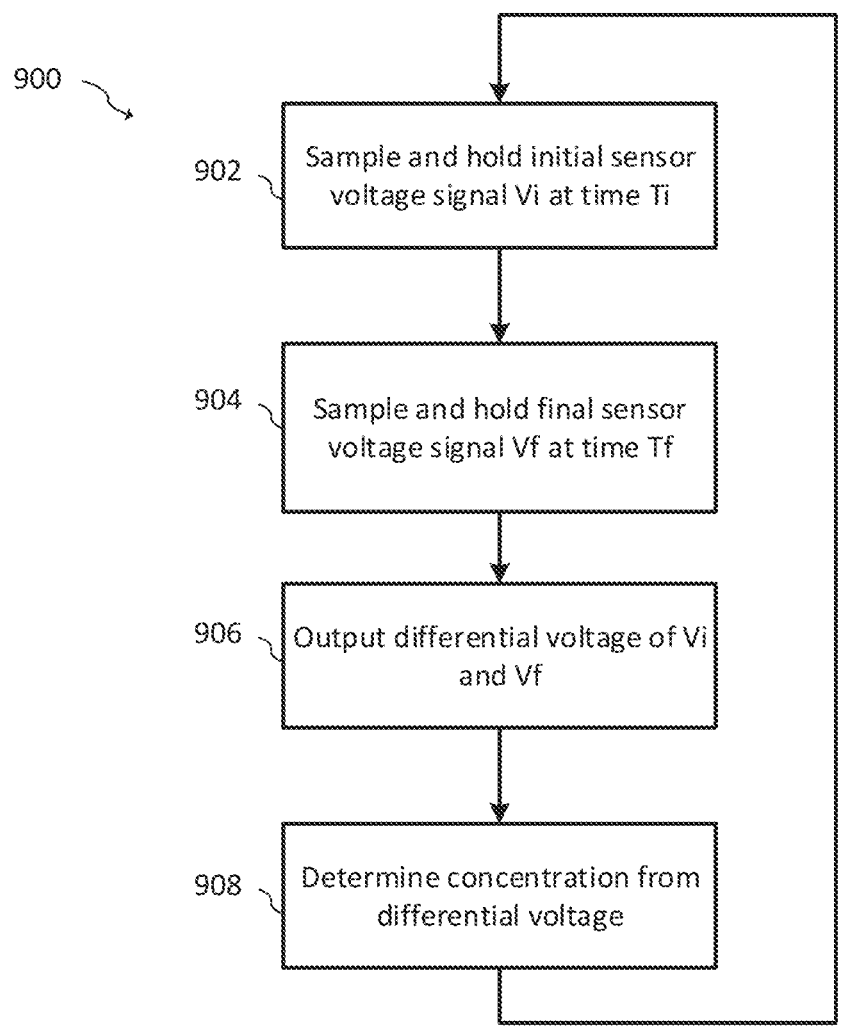
FIG. 9 illustrates a flowchart of a method for determining the concentration of a gas using a photoacoustic sensor system according to an embodiment.

FIG. 9 illustrates a flowchart of a method 900 for determining the concentration of a gas using a photoacoustic sensor system according to an embodiment. In some embodiments, the photoacoustic sensor system is similar to photoacoustic sensor system 100 shown in FIG. 1. Starting at step 902, an initial voltage Vi of a sensor signal from the photoacoustic sensor system is sampled at an initial time Ti. The initial voltage Vi may be measured using techniques described above with respect to FIG. 8. At step 904, a final voltage Vf of a sensor signal from the photoacoustic sensor system is sampled at a final time Tf. The final voltage Vf may be measured using techniques described above with respect to FIG. 8. At step 906, the different between initial voltage Vi and final voltage Vf is output as a differential voltage. The differential voltage may be determined using techniques described above with respect to FIG. 8. At step 908, the differential voltage is used to determine the concentration of the gas using a correlation between differential voltage and concentration. The correlation may be previously determined using techniques described above, particularly with respect to FIG. 5. After step 908, method 900 may be repeated starting at step 902 to determine concentrations of a gas subsequently measured by the photoacoustic sensor system.

Figure 10:
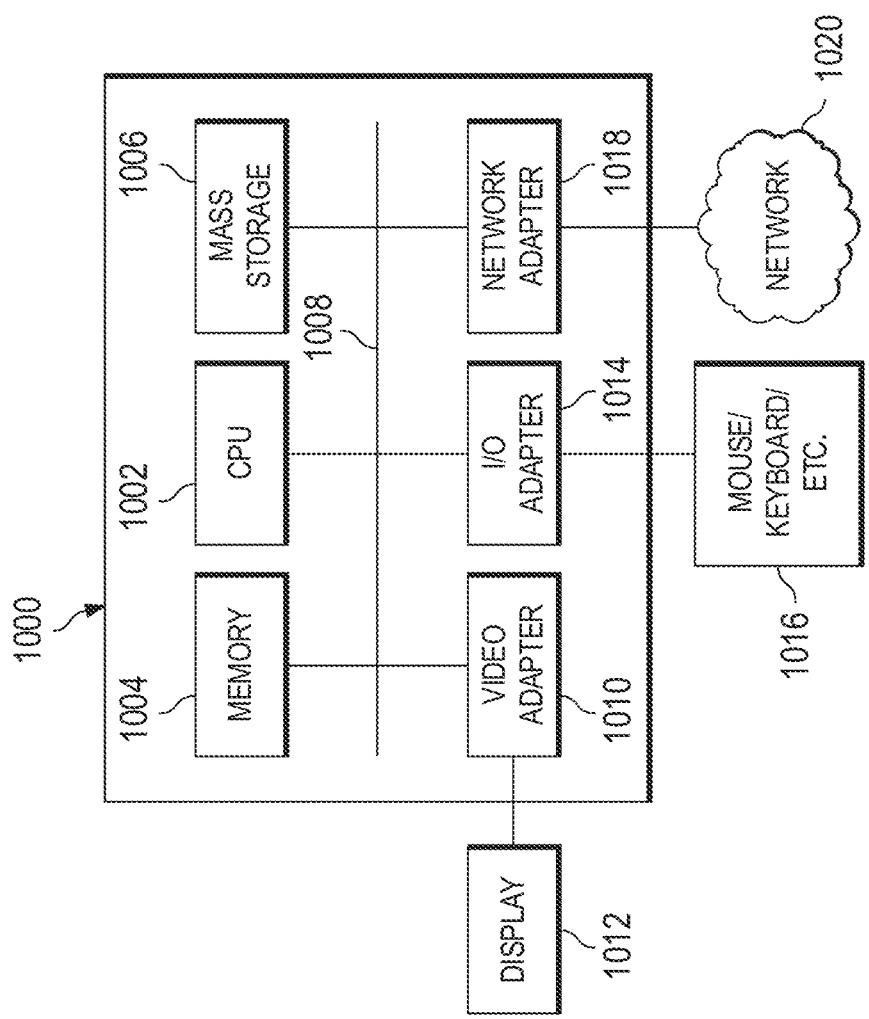
FIG. 10 illustrates a block diagram of a processing system that may be used to implement portions of embodiment photoacoustic sensor systems.

Referring now to FIG. 10, a block diagram of a processing system 1000 is provided in accordance with an embodiment of the present invention. The processing system 1000 depicts a general-purpose platform and the general components and functionality that may be used to implement portions of the embodiment radar system and/or an external computer or processing device interfaced to the embodiment radar system. The processing system 1000 may include, for example, a central processing unit (CPU) 1002, memory 1004, and a mass storage device 1006 connected to a bus 1008 configured to perform the processes discussed above. The processing system 1000 may further include, if desired or needed, a video adapter 1010 to provide connectivity to a local display 1012 and an input-output (I/O) Adapter 1014 to provide an input/output interface for one or more input/output devices 1016, such as a mouse, a keyboard, printer, tape drive, CD drive, or the like.

The processing system 1000 also includes a network interface 1018, which may be implemented using a network adaptor configured to be coupled to a wired link, such as an Ethernet cable, USB interface, or the like, and/or a wireless/cellular link for communications with a network 1020. The network interface 1018 may also comprise a suitable receiver and transmitter for wireless communications. It should be noted that the processing system 1000 may include other components. For example, the processing system 1000 may include power supplies, cables, a motherboard, removable storage media, cases, and the like. These other components, although not shown, are considered part of the processing system 1000.

According to some embodiments described herein, advantages may include faster response time of a photoacoustic sensor system. The response time of the system may be faster due to simpler or fewer calculations performed to extract information about a gas from a photoacoustic sensor signal. For example, determining a slope from two points can require significantly fewer calculations or operations than performing a Fast Fourier Transform or a curve-fitting using more than two points. The faster response time may, for example, allow for faster detection of unsafe levels of a gas in an environment. The techniques described herein may not require as much memory or as much computational power as other techniques for analyzing photoacoustic sensor signals. As such, the techniques described herein may be implemented more efficiently and using less power than other techniques. Additionally, in some cases only two data points are needed to calibrate a photoacoustic sensor system over a full useful range of detectable gas concentrations. In some cases, the techniques described herein are more robust to changes in temperature or more robust against the thermoacoustic effect than other techniques. In some cases, the techniques described herein are less affected by slow changes in gas concentration or measurement drift than other techniques. The techniques described herein may be implemented in, for example, a digital ASIC or an analog ASIC. The techniques described herein allow for filtering of acoustic ambient noise, high pressure events, spurious signals, or other unwanted signals. The techniques described herein may also be robust and linear over a large range of modulation frequencies or duty cycles.

While this invention has been described with reference to illustrative embodiments, this description is not intended to be construed in a limiting sense. Various modifications and combinations of the illustrative embodiments, as well as other embodiments of the invention, will be apparent to persons skilled in the art upon reference to the description. It is therefore intended that the appended claims encompass any such modifications or embodiments.

What is claimed is:

1. A photoacoustic gas sensor comprising:
   a chamber containing a gas;
   a pressure sensor disposed in the chamber, the pressure sensor comprising a flexible membrane and configured to output an output signal indicating a deflection of the flexible membrane;
   an emitter configured to illuminate the gas with light by being switched on at a starting time; and
   a control circuit coupled to the pressure sensor and the emitter, wherein the control circuit comprises:
      a sampling circuit configured to sample a first output signal and record a first value of the first output signal of the pressure sensor after a first duration of time from the starting time and record a second value of the first output signal of the pressure sensor after a second duration of time from the starting time for a first known gas concentration, and configured to sample a second output signal and record a first value of the second output signal of the pressure sensor after the first duration of time from the starting time and record a second value of the second output signal of the pressure sensor after the second duration of time from the starting time for a second known gas concentration, wherein the first output signal and the second output signals intersect at a common point when the output signals are superimposed or plotted together, and wherein the common point is at a third duration of time from the starting time between the first duration of time and the second duration of time;

an analysis circuit configured to determine a first slope from the first value and the second value of the first output signal, determine a second slope from the first value and the second value of the second output signal, and determine a correlation value from a difference between the first slope and the second slope divided by a difference between the first known gas concentration and the second known gas concentration; and a correlation circuit configured to receive the correlation value and apply the correlation to a third output signal that intersects with the same common point as the first and second cutout signals to determine an unknown concentration of the gas based on a slope function including the correlation value.

2. The photoacoustic gas sensor of claim 1, wherein the analysis circuit comprises an analog circuit.

3. The photoacoustic gas sensor of claim 1, wherein the gas comprises $CO_2$.

4. The photoacoustic gas sensor of claim 1, wherein the slope function comprises a linear function relating the third slope of the unknown concentration of the gas and the unknown concentration of the gas.

5. A photoacoustic gas sensor comprising:

a chamber containing a gas;

a pressure sensor disposed in the chamber, the pressure sensor comprising a flexible membrane and configured to output an output signal indicating a deflection of the flexible membrane;

an emitter configured to illuminate the gas with light; and a control circuit coupled to the pressure sensor and the emitter, wherein the control circuit is configured for receiving a first output signal from the pressure sensor, the first output signal associated with a first concentration of the gas; receiving a second output signal from the pressure sensor, the second output signal associated with a second concentration of the gas; determining a first slope of the first output signal from a first value of the first output signal at a first indication of time and a second value of the first output signal at a second indication of time; determining a second slope of the second output signal from a first value of the second output signal at the first indication of time and a second value of the second output signal at the second indication of time; and determining a correlation between a slope of an output signal and a known concentration of the gas based on a difference between the first slope and the second slope divided by a difference between the first concentration and the second concentration, wherein the first output signal and the second output signal comprise different output signals having different values at the first indication of time, having different values at the second indication of time, and having a same value at a third indication of time between the first indication of time and the second indication of time, and wherein the first output signal and the second output signal intersect at a common point corresponding to the same value when the output signals are superimposed or plotted together, and wherein the common point is located at the third indication of time.

6. The photoacoustic gas sensor of claim 5, wherein the gas comprises $CO_2$.

7. The photoacoustic gas sensor of claim 5, wherein the pressure sensor comprises a flexible membrane, and the first output signal corresponds to an amount of deflection of the flexible membrane.

8. The photoacoustic gas sensor of claim 5, wherein the control circuit is further configured for determining the correlation comprises determining parameters of a linear relationship of the correlation including a correlation slope and a correlation y-intercept.

9. The photoacoustic gas sensor of claim 5, wherein the control circuit is further configured for receiving the third output signal from the pressure sensor; determining a third slope of the third output signal from a first value of the third output signal at the first indication of time and a second value of the third output signal at the second indication of time; and determining a third concentration of the gas associated with the third output signal based on the third slope and the correlation.

10. The photoacoustic gas sensor of claim 9, wherein the control circuit is configured for determining the third slope of the third output signal by summing the third output signal with at least one additional output signal.

11. The photoacoustic gas sensor of claim 9, wherein the control circuit is configured for comparing a difference between the first value of the third output signal and a first value of a fourth output signal with a threshold value.

12. The photoacoustic gas sensor of claim 5, wherein the control circuit comprises a sampling circuit.

13. The photoacoustic gas sensor of claim 5, wherein the control circuit comprises an analysis circuit.

14. The photoacoustic gas sensor of claim 13, wherein the analysis circuit comprises an analog circuit.

15. The photoacoustic gas sensor of claim 5, wherein the control circuit comprises a correlation circuit.

* * * * *

UNITED STATES PATENT AND TRADEMARK OFFICE
CERTIFICATE OF CORRECTION

PATENT NO. : 11,415,559 B2  
APPLICATION NO. : 16/654087  
DATED : August 16, 2022  
INVENTOR(S) : David Tumpold et al.

Page 1 of 1

It is certified that error appears in the above-identified patent and that said Letters Patent is hereby corrected as shown below:

In the Claims

Claim 1, Column 17, Line 23; delete "cutout" and insert --output--.

Signed and Sealed this
Twenty-seventh Day of September, 2022

Katherine Kelly Vidal
*Director of the United States Patent and Trademark Office*